(12) United States Patent
Braig et al.

(10) Patent No.: US 6,645,142 B2
(45) Date of Patent: Nov. 11, 2003

(54) GLUCOSE MONITORING INSTRUMENT HAVING NETWORK CONNECTIVITY

(75) Inventors: James R. Braig, Piedmont, CA (US); Gary E. Hewett, Castro Valley, CA (US); Michael A. Munrow, Belmont, CA (US); Julian M. Cortella, Alameda, CA (US); Kamrava Azizi, San Ramon, CA (US); Daniel S. Goldberger, Boulder, CO (US)

(73) Assignee: OptiScan Biomedical Corporation, Alameda, CA (US)

( * ) Notice: Subject to any disclaimer, the term of this patent is extended or adjusted under 35 U.S.C. 154(b) by 93 days.

(21) Appl. No.: 09/728,743

(22) Filed: Dec. 1, 2000

(65) Prior Publication Data

US 2002/0068858 A1 Jun. 6, 2002

(51) Int. Cl.⁷ ............................. A61B 5/00; G08B 23/00
(52) U.S. Cl. ..................... 600/300; 600/316; 128/903; 128/904; 340/501
(58) Field of Search ................................ 600/300, 301, 600/316, 347, 365; 128/903, 904; 340/501, 825.28

(56) References Cited

U.S. PATENT DOCUMENTS

| | | | | |
|---|---|---|---|---|
| 5,019,974 A | * | 5/1991 | Beckers ...................... 600/316 |
| 5,615,672 A | * | 4/1997 | Braig et al. .................. 600/474 |
| 5,966,654 A | * | 10/1999 | Croughwell et al. ... 340/825.28 |
| 5,967,975 A | * | 10/1999 | Ridgeway .................... 600/300 |
| 6,248,067 B1 | * | 6/2001 | Causey et al. ............... 128/903 |
| 6,295,506 B1 | * | 9/2001 | Heinonen et al. ........... 600/301 |
| 6,377,894 B1 | | 4/2002 | Deweese et al. |
| 6,379,301 B1 | * | 4/2002 | Worthington et al. ....... 600/300 |
| 6,413,213 B1 | | 7/2002 | Essenpreis et al. |
| 2001/0031913 A1 | | 10/2001 | Ito et al. |
| 2002/0082797 A1 | | 6/2002 | Deweese et al. |

FOREIGN PATENT DOCUMENTS

| | | |
|---|---|---|
| EP | 0 970 655 A1 | 1/2000 |
| WO | WO 99/25110 | 5/1999 |
| WO | WO 00/28460 | 5/2000 |
| WO | WO 00/32258 | 6/2000 |
| WO | WO 00/53085 | 9/2000 |

OTHER PUBLICATIONS

Design Feature; "Low–Cost Techniques Bring Internet Connectivity To Embeded Device", EDN, Nov. 11, 1999; NS Manju Nath, Technical Editor; (5 pages).

* cited by examiner

Primary Examiner—Eric F. Winakur
Assistant Examiner—David J. McCrosky
(74) Attorney, Agent, or Firm—Knobbe, Martens, Olson & Bear, LLP

(57) ABSTRACT

A glucose monitoring instrument having network-based communication features which provide a link between patient and practitioner. The glucose monitoring instrument comprises circuitry for communicating data with one or more destination sites on the network which are configured to transmit and receive information to and from the instrument. Instrument measurements are transmitted over the link in addition to information and guidance, to provide increased accuracy, improved program compliance, and patient guidance from a supervisory authority or medical practitioner. In addition, a set of calibration features encourage calibration compliance.

8 Claims, 3 Drawing Sheets

GLUCOSE MONITORING INSTRUMENT HAVING NETWORK CONNECTIVITY

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to medical equipment for measuring blood glucose levels, and more particularly to a blood glucose measuring instrument having internet-based communication features.

2. Description of the Background Art

A patient, having been taught how to use an existing portable glucose monitor is generally required thereafter to independently conduct and record their own measurements. Furthermore, the patient typically is required to both record and assess the measurements without benefit from their practitioner or a supervising authority. Numerous errors can arise from these unsupervised procedures that may result in serious health risks for patients which knowingly, or inadvertently, are not in compliance with medical directives.

Typically, patients using a glucose monitor are given a schedule of measurements to be complied with and a notebook in which to record the measurements. Patients often forget, or in some instances forego, conducting and correctly recording their glucose levels as measured by the instrument. If a patient skips a measurement they may even elect to write down a "likely" number in the notebook as if such a measurement had been taken. Patient interaction with such a manual glucose monitoring instrument therefore provides no assurance of correct measurement and recordation. Furthermore, patients in a myriad of situations may require additional information and assistance with regard to the use and maintenance of their glucose measurement instrument.

In addition, to assure glucose measurement accuracy, a measuring instrument may require periodic calibration and assuring calibration compliance on instruments in the field is burdensome.

Therefore, a need exists for a glucose monitoring system that provides a link between the patient and the practitioner to encourage compliance and facilitate equipment calibration. The present invention satisfies those needs, as well as others, and overcomes deficiencies in current monitoring systems and procedures.

BRIEF SUMMARY OF THE INVENTION

The present invention is a glucose monitoring device with remote communications capabilities. According to an aspect of the invention, a data link is provided between the equipment and a centralized station, or server. The centralized station can monitor important information, such as: equipment calibration, the diligence of a patient taking and recording measurements according to a schedule, and the actual measurements taken by the patient. The centralized station is preferably capable of forwarding information to the patient's physician for evaluation. In addition, the centralized station can have optional capability of locking out the patient if the patient has not paid his or her bills. According to another aspect of the invention, the information is communicated from the glucose monitor directly to the physician. As can be seen, therefore, the invention links the monitoring activities performed by the patient and the assessment of those activities by the physician while reducing the chance of human error introduced into the long-term monitoring and treatment process.

By way of example, and not of limitation, a non-invasive subsurface spectrophotometer instrument equipped with a communications link according to the invention takes the glucose measurements and communicates them over a network, such as the internet. The spectrophotometer instrument comprises data communication circuitry, such as dial-up circuitry, and additional session control protocols which integrate a number of the functions within the instrument for communication over a network connection. A destination site, or sites, on the network are configured to receive information from the instrument and to transmit information and services.

An object of the invention is to provide a link from patient to practitioner over which timely communication of pertinent glucose monitoring information can travel.

Another object of the invention is to provide for remote monitoring of patient compliance.

Another object of the invention is to provide for remote equipment monitoring and calibration by a central station.

Another object of the invention is to provide for periodic transmission of measurement results.

Another object of the invention is to provide network communication over a standardized communications interface.

Another object of the invention is to provide a communications structure which can support data encryption.

Another object of the invention is to aid compliance by alerting the patient, by sound or visual cues, when the time arrives to conduct a measurement.

Another object of the invention is to reduce human error in conducting and recording measurements.

Another object of the invention is to eliminate secretive non-compliance, wherein a patient enters fictional measurement data into the measurement log.

Another object of the invention is to provide the capability of generating programmed practitioner warnings when measurements fall outside the bounds of a selected range.

Another object of the invention is to provide a panic button which allows a concerned patient to alert their practitioner.

Another object of the invention is to engender practical practitioner guidance to patients.

Another object of the invention is to allow the instrument manufacturer to track compliance and calibration of the glucose monitoring instrument.

Another object of the invention is to provide an accurate database that may be used by insurance and pharmaceutical companies.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are provided for illustrative purposes only.

DETAILED DESCRIPTION OF THE INVENTION

Figure 1:
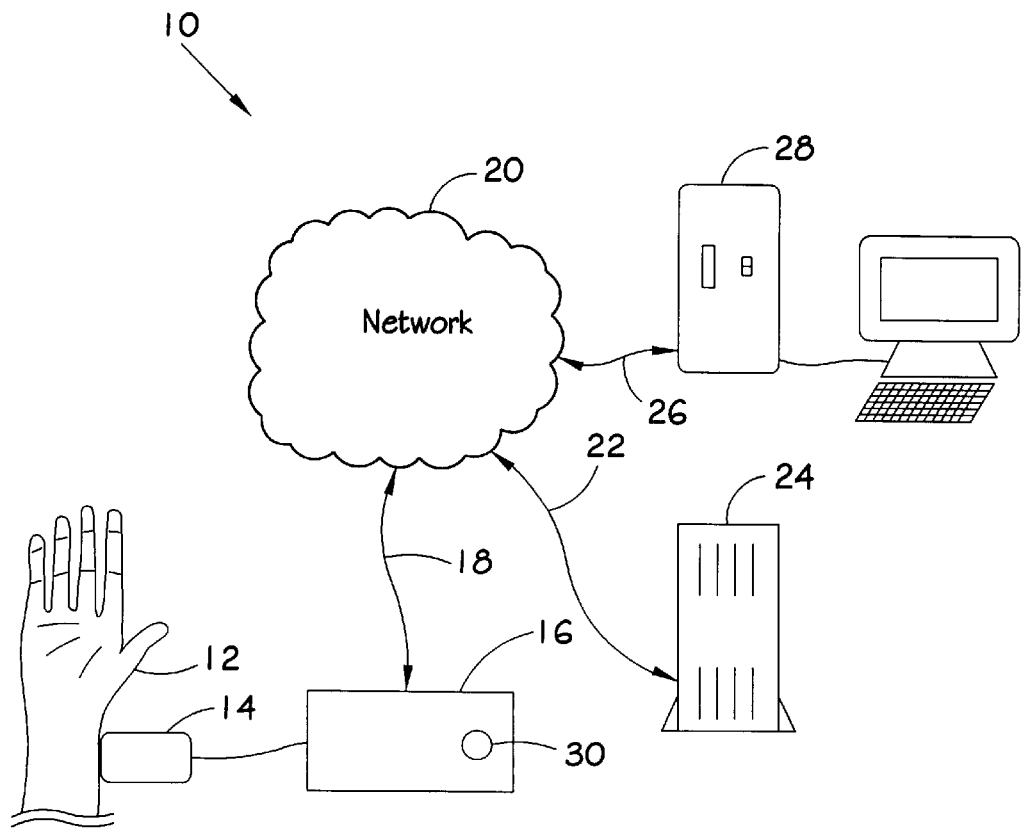
FIG. 1 is a functional block diagram showing a glucose monitoring system with network connectivity according to the present invention.
Figure 2:
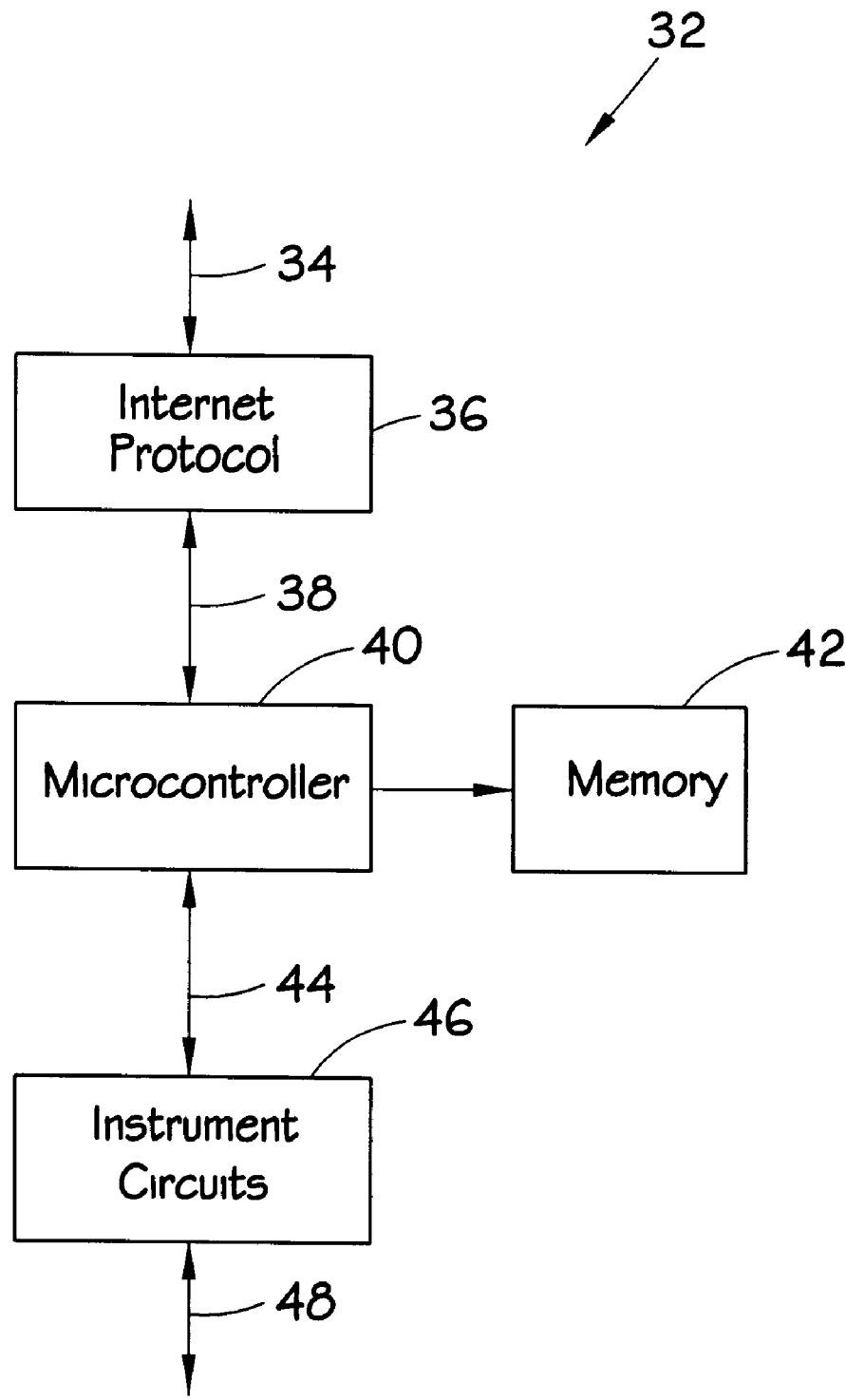
FIG. 2 is a block diagram of the electronic circuits within the glucose monitoring system of FIG. 1.
Figure 3:
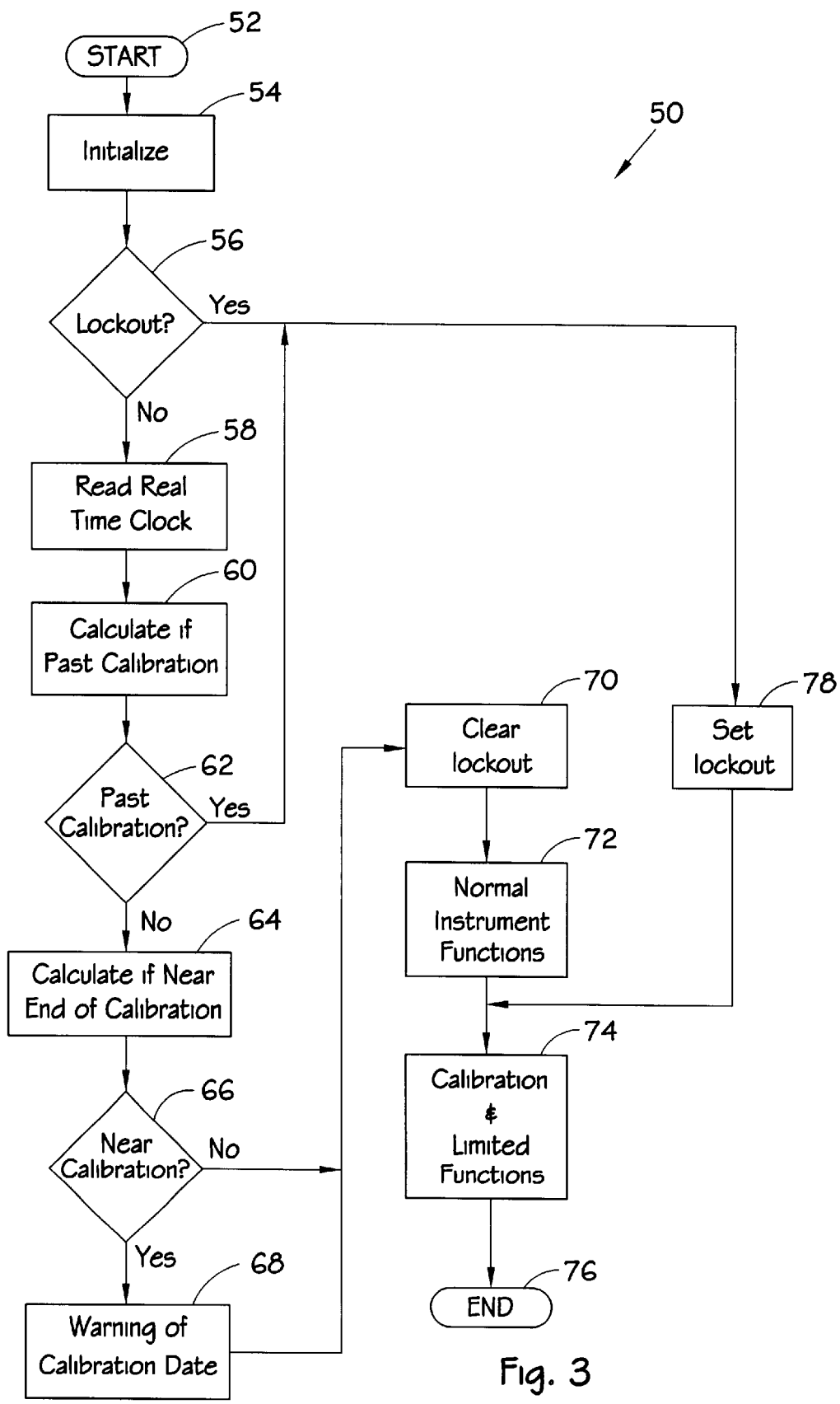
FIG. 3 is a flowchart exemplifying calibration lockout according to one aspect of the present invention.

Referring more specifically to the drawings for illustrative purposes, the present invention is embodied in the system generally shown in FIG. 1 through FIG. 3. It will be appreciated that the system may vary as to configuration and as to details of the parts, and that the method may vary as to the specific steps and sequence, without departing from the basic concepts as disclosed herein.

Referring to FIG. 1, a glucose monitoring system 10 is shown connected to remote stations over a network. The hand of a patient 12 is shown positioned to allow a measurement to be performed by glucose detector element 14 which is capable of taking non-invasive measurements of bodily glucose levels. Preferably, measurement element 14 comprises a thermal gradient detector such as a spectrophotometer. A signal processing system 16 of the instrument collects the measurements from detector 14 and processes the data into a set of results. It will be appreciated that the instrument preferably includes input and output devices, such as a display and a set of control inputs (not shown) for communicating information directly to and from the patient. The combination of detector 14 and processor 16 form a complete non-invasive glucose measuring device that typically would be used in the home of a patient. Examples of glucose monitoring equipment without internet connectivity are described in U.S. Pat. No. 5,900,632 to Sterling et al. and U.S. Pat. No. 5,615,672 to Braig et al., which are both incorporated herein by reference. In accordance with the present invention, however, the signal processing system is equipped with a network interface along with one or more processing elements for processing the measurement signals and for control of network communications.

Data is communicated over the network as determined by the configuration of the system and the state and condition of the measurement being performed. Measurement data may accordingly be communicated to a remote station at the time the measurement is performed, or it may be retained within the instrument and sent to the remote station according to a schedule or other selection criterion. The instrument is capable of comparing each measurement with a set of limits and providing alerts to a supervisory authority regarding excursions therefrom. In FIG. 1 the measurement data is shown being routed through a connection 18 to the internet 20, whose destination is routed through connection 22 to a centralized monitoring computer 24, or a server. The centralized computer is preferably capable of checking the data for emergency conditions and logging the data for later use. In addition, the centralized computer may monitor equipment status for proper operation and calibration. It will be appreciated that multiple servers, or centralized stations, can be provided for communicating with the blood glucose instruments. Furthermore, the centralized computer may transfer or simultaneously route the data via connection 26 to a computer 28 in the office of a medical practitioner over the internet. Alternatively, the data may be directly sent over the internet to an associated medical practitioner 28 from processor 16. It will be appreciated that the foregoing data routing is provided as an example, and not as a limitation, of the data routing utilized to provide the internet services as described according to the invention. Preferably a panic button 30 provides the patient with a mechanism for alerting a medical practitioner should an important concern arise. In addition, sound and/or visual output is preferably provided by the instrument for signaling the patient when the time arrives to perform a measurement, or of a directive from a supervisory authority as received over the internet.

The present invention, as described herein, provides either a direct or indirect link from the patient to the practitioner. The practitioner is thereby accorded an ability to monitor the status of the patient and may elect to be alerted should deviations in the measurement values or timeliness arise. The system may be configured to transmit measurement data at predetermined intervals, or at the time each measurement is performed. The measurements can be transmitted using various network protocols which include standard internet protocols, encrypted protocols, or email protocols.

In the preferred embodiment of the invention, processor 16 is additionally capable of providing visual or audible cues to the patient when the time arrives to conduct a measurement. These alerts may be augmented by requests, over the internet link of the instrument, from the practitioner. Errors introduced within measurements and recordation within a manual system can thereby be eliminated with the electronically logged measurements. It will be appreciated that the system provides enhanced utility and measurement credibility over the use of an instrument that requires manual logging of the measurements and no practitioner interaction thereof.

Secretive non-compliance may also be eliminated as the patient is not conferred the responsibility of manually logging measurements. In using the instrument according to the present invention, the measurements collected within the instrument by the patient are capable of being transmitted to the practitioner, or centralized station, such that if a patient is not being diligent in conducting measurements, the practitioner may immediately contact the patient to reinforce the need for compliance. In addition, the information provided over the network can be used to warn the practitioner when measurement readings appear abnormal, so that the practitioner may then investigate the situation and verify the status of the patient.

It will be appreciated that the invention has particular utility for patients preferring to receive direct guidance from a practitioner. The information that flows between the patient and the practitioner increases the ability of the practitioner to provide knowledgeable patient guidance.

FIG. 2 illustrates the functional blocks of an embodiment of circuitry 32 for implementing the signal processing hardware 16 shown in FIG. 1. A network connection 34 connects to a network processing circuit, exemplified by an Internet Protocol (IP) circuit or processor 36. Numerous circuits are available for providing internet connectivity, such as the SX-Stack™ chip from Scenix Semiconductor, and the iChip™ from Connect One Electronics. These integrated circuit chips and other available chips provide interface layers for supporting a Transmission Control Protocol/Internet Protocol (TCP/IP). The internet protocol chip 36 has an interface 38 with a control processor section 40, which preferably comprises microcontroller or like. Control processor section 40 in turn has access to conventional memory 42. To provide security and fault tolerance of the instrument it is preferable for the control processor, or the internet protocol circuit, to encrypt and provide verification strings or tokens within the data being sent across the network, and accordingly to decrypt information being received and verify the received strings or tokens. The control processor 40 has an interface 44 with the instrumentation circuits 46, which is in turn configured with an interface 48 to the glucose detection element 14 shown in FIG. 1.

The network link provides a mechanism to facilitate performing and recording glucose measurements under supervision, while it additionally provides for periodic instrument calibration, and the ability to assure both measurement and calibration compliance. Calibration data can be communicated from instruments in the field to the instrument manufacturer, or a service organization, so that instruments and their calibrations may be logged. The disclosed network link can be utilized to provide various mechanisms for assuring calibration compliance. Generally the mechanisms are of two categories, those that provide information or a warning about calibration, and those that prevent use of an instrument which is out of calibration. Preferably instruments which have exceeded their calibration interval, or schedule, are to be locked out from further use until recalibration is performed. For example, the instrument may be set to operate for thirteen months for a given calibration interval of twelve months. The unit preferably issues warnings prior to the expiration of calibration, and warnings of increased severity after the expiration of the calibration interval. If the unit, however, is not properly calibrated by the end of the thirteen months, normal operation ceases, thereby locking out the user after providing an appropriate error message in regard to the expired calibration. Upon recalibration, the calibrated operation interval is restored to provide for another thirteen month period of calibrated operation.

Alternatively, or in addition thereto, a "lockout command" can be sent to the unit over the communication link from the manufacturer which engages a lockout mode of the device, so that continued operation may not be continued until the unit has been serviced. The lockout command could also be sent in the event that the patient has not paid his or her bills, or be sent under other circumstances warranting lockout of the instrument.

Another mode is that of locking out normal instrument use after the expiration of calibration, and allowing limited use thereafter only after a code, or token, has been downloaded from a supervisory site. Although many variations are possible, the code could for instance be provided when a calibration appointment is made for the instrument. To provide continued service and minimize cost, the patient may be allowed to perform calibration checks of the instrument. The patient is supplied with a small set of glucose calibration standards which are read by the instrument once it is put into a calibration mode and preferable connected to a remote site for supervising the process. Should the calibration check pass, wherein the instrument readings fall within normal levels, or be capable of being automatically adjusted thereto, the calibration interval may be extended. Failure of the calibration check would typically necessitate returning the instrument for service.

FIG. 3 illustrates an embodiment of a process 50 for assuring calibration compliance within the glucose measurement instrument by utilizing a lockout mechanism. The programmed instructions associated with the glucose measurement instrument are started at block 52 and initialized at block 54, and a check is made on a lockout flag at block 56 to determine if it was set during a prior session by a command received from the internet, or due to being out of calibration. Not having been locked out from a prior session, the real-time clock (RTC) of the device is read at block 58 and a calculation is performed at block 60 comparing the current date with the stored calibration date and calibration interval. If upon checking calibration at block 62 the calibration interval has not yet expired, then a calculation is performed at block 64 comparing the current date with the stored calibration date and near-calibration interval. Near-calibration is checked at block 66 and, if calibration is to expire soon, then a user warning is issued at block 68, preferably informing the user of the date of the upcoming expiration of the calibration interval. The lockout flag is cleared at block 70 and processing within the glucose measurement instrument continues with normal instrument functions being accessible at block 72, along with calibration and other limited functions at block 74, until the user shuts down the instrument and processing ends at block 76. If the lockout flag was set from a prior instrument operation, or the calibration interval was exceeded, then a lockout flag would be set at block 78, and the instrument functionality would thereby be restricted to execution of the calibration procedures and other limited functions at block 78 while the normal instrument functionality would not be accessible. The calibration procedure itself may be augmented and improved by providing interaction between the servicing party and the manufacturer, such interaction may include providing guidance information to the servicing party, and the collection of measurement information by the manufacturer.

An optional feature of the invention would be to provide for lockout of the glucose monitor and/or.

It will be appreciated that the present invention provides functionality beyond that which can be provided by a stand-alone glucose measurement instrument, as the practitioner, or practitioners office, is brought back into the glucose measurement process to confer a portion of the benefits normally associated with an office visit. It will be recognized that although not providing equivalent results, the features described for the embodiment of a non-invasive glucose monitoring instrument are generally applicable to glucose monitoring hardware in which invasive measurements are taken. The aforesaid description of the invention illustrates how these features provide the capability for two-way data flow which facilitates the conducting and recording of correct measurements while encouraging compliance in regard to both measurements and instrument calibration. Furthermore, the data collected by the system may be utilized by others in addition to the practitioner, such as pharmaceutical companies which may be provided data access to alter or administer medication programs, and insurance companies which may require data regarding patient diligence according to the specified treatment program.

Accordingly, it will be seen that the present invention provides numerous benefits for patients needing to closely monitor blood glucose levels and it can be implemented with numerous variations and alternatives obvious to those skilled in the art.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A glucose monitoring system adapted for remote but direct supervision of a patient's monitoring activities by a medical practitioner, comprising:

a glucose monitoring network; and a glucose monitoring device for use by the patient, the glucose monitoring device comprising:

a glucose detection element for collecting a patient signal proportional to a glucose level of the patient;

an instrument circuit for processing the patient signal to determine a glucose measurement for the patient;

a network interface coupled with the glucose monitoring network; and a networking circuit coupled with the network interface, the network circuit comprising: an interface coupled with the instrument circuit;

a memory for storing the glucose measurement; and a processor coupled with the interface and with the memory, the processor configured to send the glucose measurement over the glucose monitoring network to permit the measurement to be monitored by the medical practitioner, the processor further configured to respond to a lockout command received over the network by placing the glucose monitoring device in a lockout mode in which glucose measurement functionality is not accessible to the patient, and wherein calibration functionality of the glucose monitoring device remains accessible to the patient when the glucose monitoring device is in the lockout mode, such that the patient may follow a calibration procedure to recalibrate and unlock the glucose monitoring device.

2. A glucose monitoring device for use by a patient, comprising:

detection circuitry capable of generating glucose measurements reflective of the patient's glucose level;

a processor connected to the detection circuitry; and a network interface that couples the processor to a network;

wherein the processor is configured to send the glucose measurements over the network to permit such measurements to be monitored at a central monitoring facility, and is further configured to respond to at least one type of command received over the network by modifying a mode of operation of the glucose monitoring device, and wherein calibration functionality of the device remains accessible to the patient when the device is in a lockout mode in which glucose measurement functionality is not accessible to the patient, such that the patient may follow a calibration procedure to recalibrate and unlock the device.

3. The glucose monitoring device of claim 2, wherein the processor is responsive to a command received from the network by issuing a warning to the user indicating that a calibration interval will end in a preset time.

4. A method of monitoring glucose levels of a patient, comprising:

obtaining glucose measurements of the patient with a portable glucose measurement device;

transmitting the glucose measurements of the patient over a network from the glucose measurement device to a central monitoring facility to permit the measurements to be monitored by a practitioner; and transmitting a command over the network to the portable glucose measurement device representing a signal to the user that signifies a change in a mode of operation of the device, wherein the command is a lockout command that places the device in a lockout mode in which glucose measurement functionality is not accessible to the patient and but in which calibration functionality of the device remains accessible to the patient, such that the patient may follow a calibration procedure to recalibrate and unlock the device.

5. A method of monitoring glucose levels of a patient, comprising:

obtaining glucose measurements of the patient with a portable glucose measurement device;

transmitting the glucose measurements of the patient over a network from the glucose measurement device to a central monitoring facility to permit the measurements to be monitored by a practitioner; and transmitting a command over the network to the portable glucose measurement device representing a signal to the user that signifies a change in a mode of operation of the device, wherein the command is a lockout command that places the device in a lockout mode in which glucose measurement functionality is not accessible to the patient, and wherein the lockout command is transmitted in response to detection that the device has not been calibrated within a selected period of time.

6. The method of claim 5, further comprising displaying a calibration expiration warning at the glucose measurement device prior to the selected period of time.

7. A method of monitoring glucose levels of a patient, comprising:

obtaining glucose measurements of the patient with a portable glucose measurement device;

transmitting the glucose measurements of the patient over a network from the glucose measurement device to a central monitoring facility to permit the measurements to be monitored by a practitioner; and transmitting a command over the network to the portable glucose measurement device representing a signal to the user that signifies a change in a mode of operation of the device, wherein the command is a lockout command that places the device in a lockout mode in which glucose measurement functionality is not accessible to the patient, and wherein the lockout command is transmitted in response to detection that the device requires service.

8. A method of monitoring glucose levels of a patient, comprising:

obtaining glucose measurements of the patient with a portable glucose measurement device;

transmitting the glucose measurements of the patient over a network from the glucose measurement device to a central monitoring facility to permit the measurements to be monitored by a practitioner;

transmitting a command over the network to the portable glucose measurement device representing a signal to the user that signifies a change in a mode of operation of the device; and displaying a calibration expiration warning at the glucose measurement within a selected period of time.

* * * * *